United States Patent [19]

Sas et al.

[11] Patent Number: 5,037,817

[45] Date of Patent: Aug. 6, 1991

[54] PHARMACEUTICAL COMPOSITION WHICH CONTAINS A PHARMACEUTICALLY SUITABLE CARRIER AND THE COMPOUND HAVING THE STRUCTURE (7α,17α)-17-HYDROXY-7-METHYL-19-NOR-17-PREGN-5(10)-EN-20-YN-3-ONE

[75] Inventors: Gerard A. J. M. T. Sas; Emile M. van Doornum, both of Oss, Netherlands

[73] Assignee: Akzo N.V., Arnhem, Netherlands

[21] Appl. No.: 494,089

[22] Filed: Mar. 15, 1990

[30] Foreign Application Priority Data

Mar. 18, 1989 [NL] Netherlands ............ 89.00673

[51] Int. Cl.$^5$ .............................................. A61K 31/56
[52] U.S. Cl. .................................... 514/177; 514/178; 552/597
[58] Field of Search ...................... 514/169–182, 514/177, 178; 260/397.4

[56] References Cited

U.S. PATENT DOCUMENTS

| | | | |
|---|---|---|---|
| 3,340,279 | 9/1967 | de Jongh et al. | 260/397.4 |
| 4,273,710 | 6/1981 | Jones et al. | 260/239.55 |
| 4,391,755 | 7/1983 | Wang et al. | 260/397.45 |
| 4,447,426 | 5/1984 | Wang et al. | 260/397.45 |
| 4,701,450 | 10/1987 | Kelder et al. | 514/177 |
| 4,933,168 | 6/1990 | Jones et al. | 514/174 |

OTHER PUBLICATIONS

De Clerc et al, Chem. Abstr. 101: 72994d (1984).
Van Vliet et al., Chem. Abstr. 105: 209261s (1986).
Haleblian et al, J. Pharm. Sci. 58(8): 911–929, Aug. 1969, "Pharmaceutical Applications of Polymorphism".

*Primary Examiner*—Shep K. Rose
*Attorney, Agent, or Firm*—William M. Blackstone

[57] ABSTRACT

A pharmaceutical composition which contains a pharmaceutically suitable carrier and the compound having the structure (7α,17α)-17-hydroxy-7-methyl-19-nor-17-pregn-5(10)-en-20-yn-3-one, characterized in that the said compound is crystalline pure and completely or virtually completely free from the other crystalline form.

9 Claims, 6 Drawing Sheets

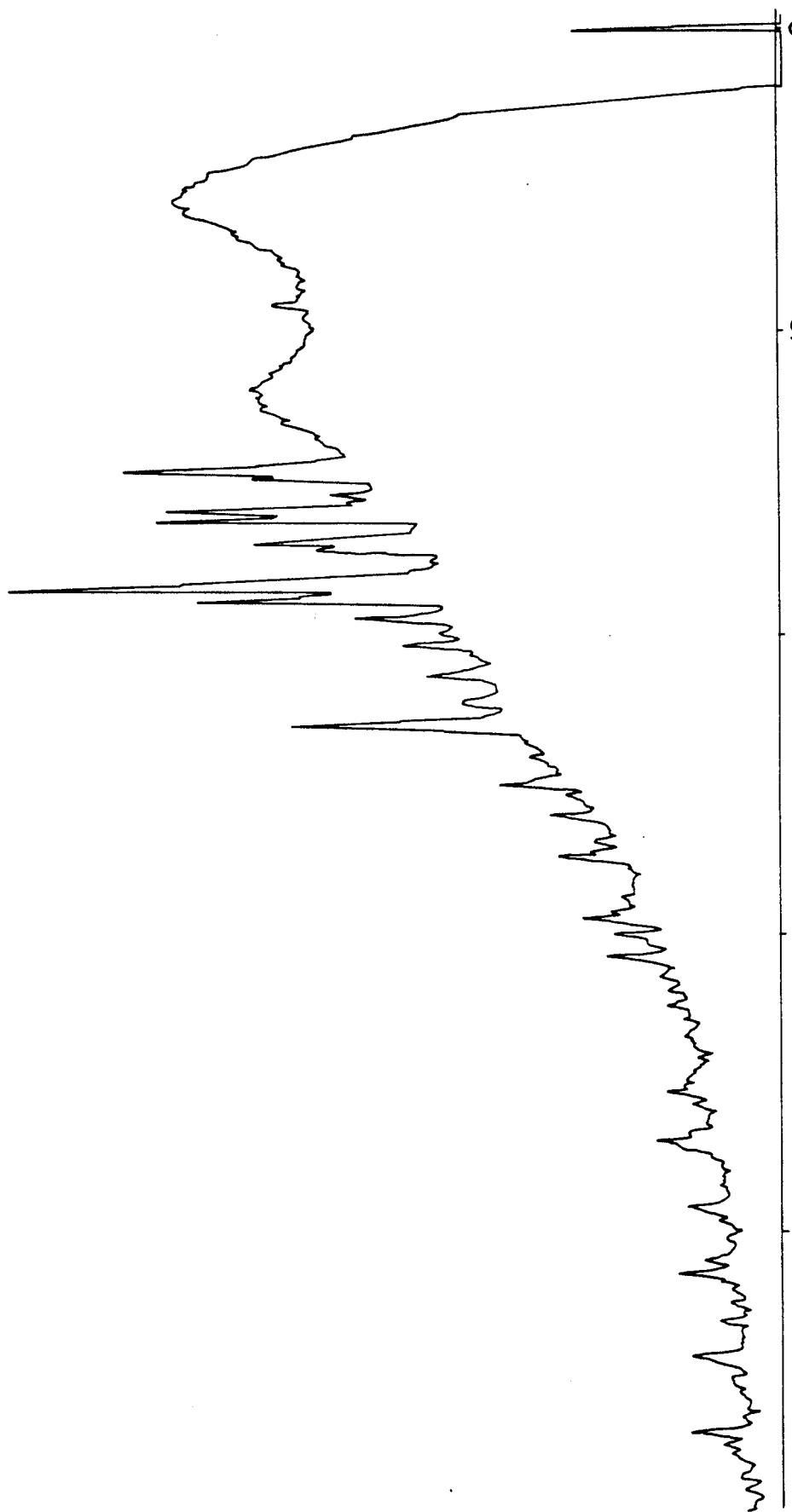
FIG.1: POWDER X-RAY DIFFRACTION SPECTRUM OF FORM I

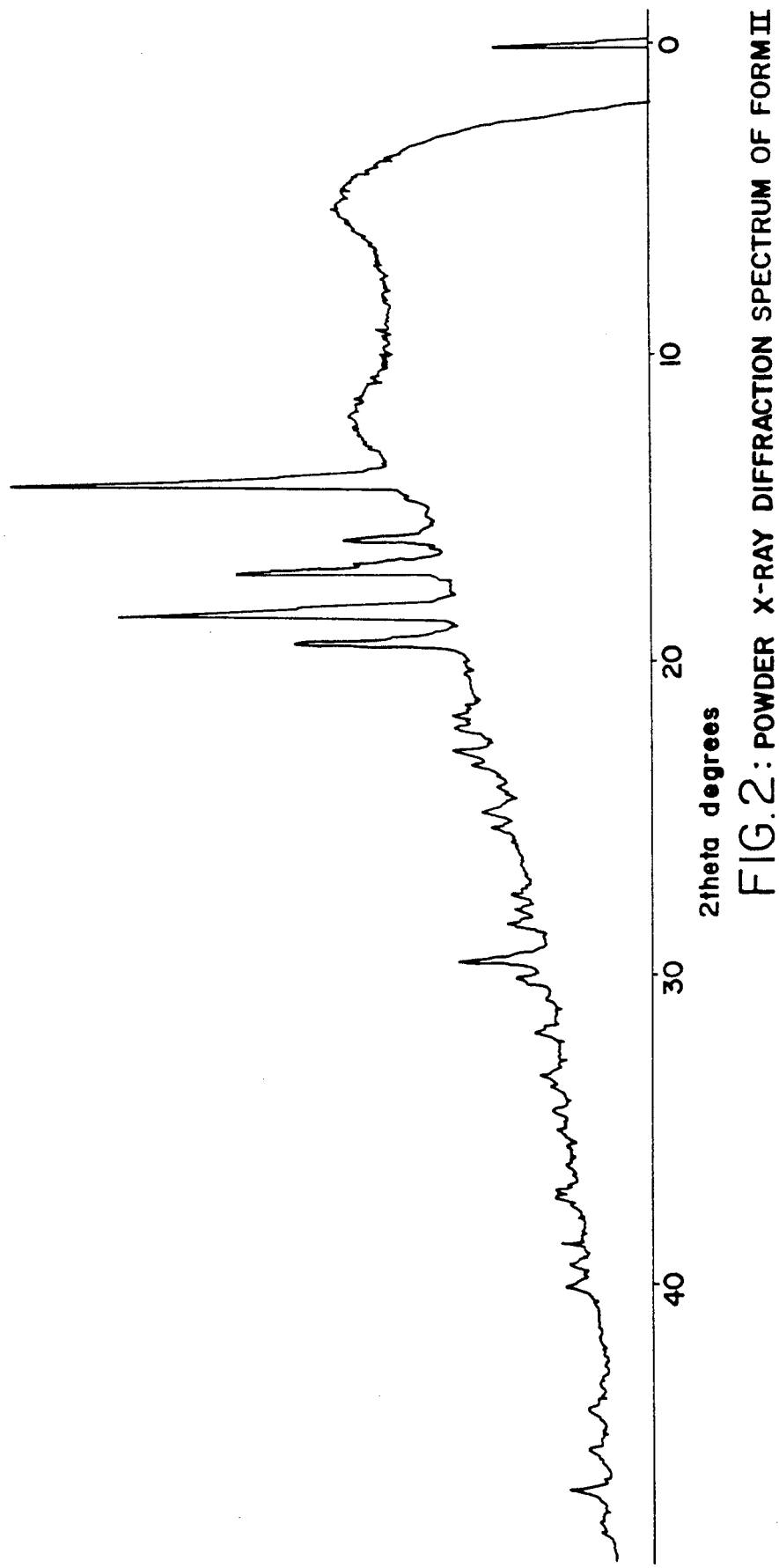

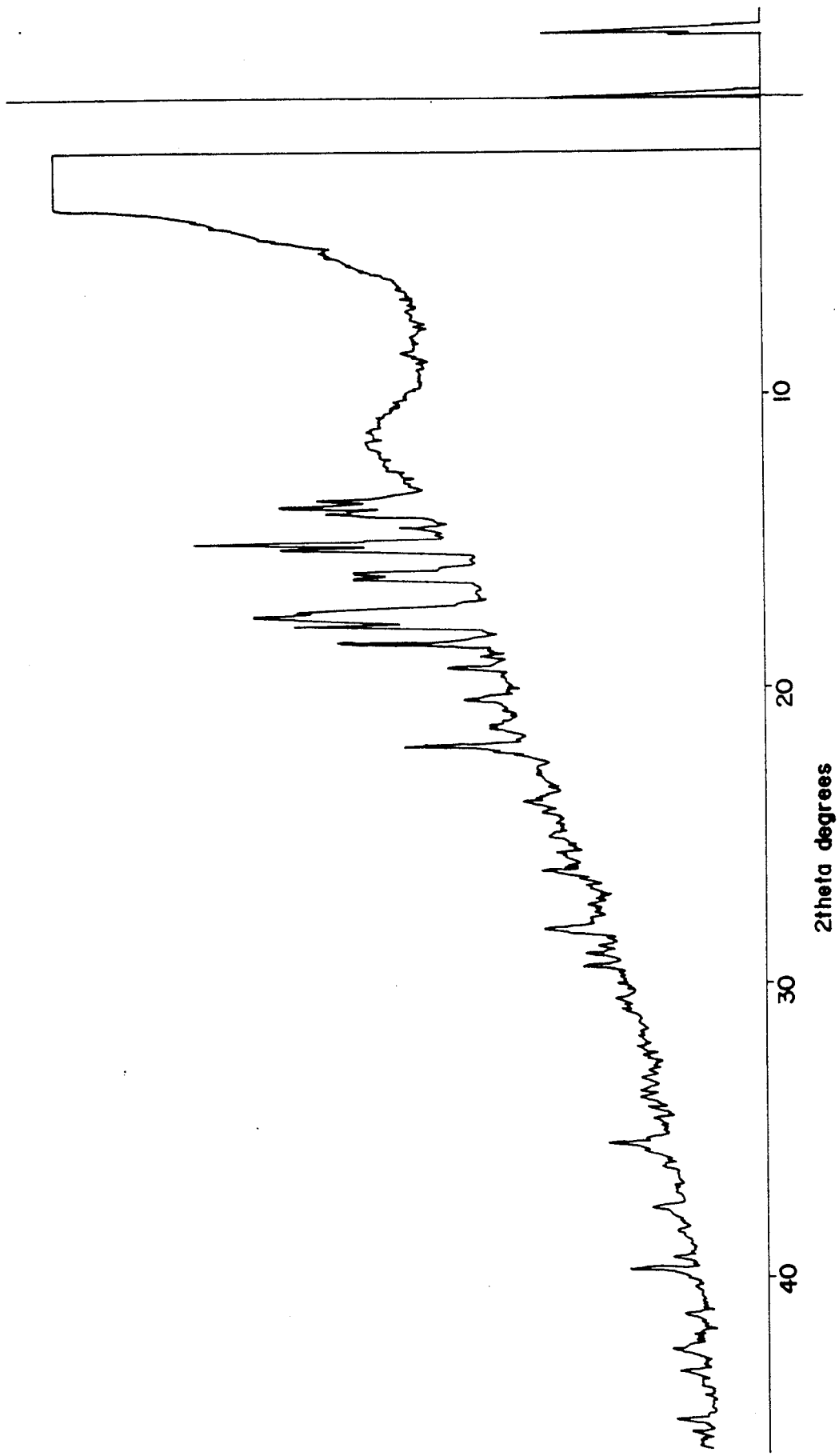
FIG.3: POWDER X-RAY DIFFRACTION SPECTRUM OF A MIXTURE OF 57.5% OF FORM I AND 42.5% OF FORM II

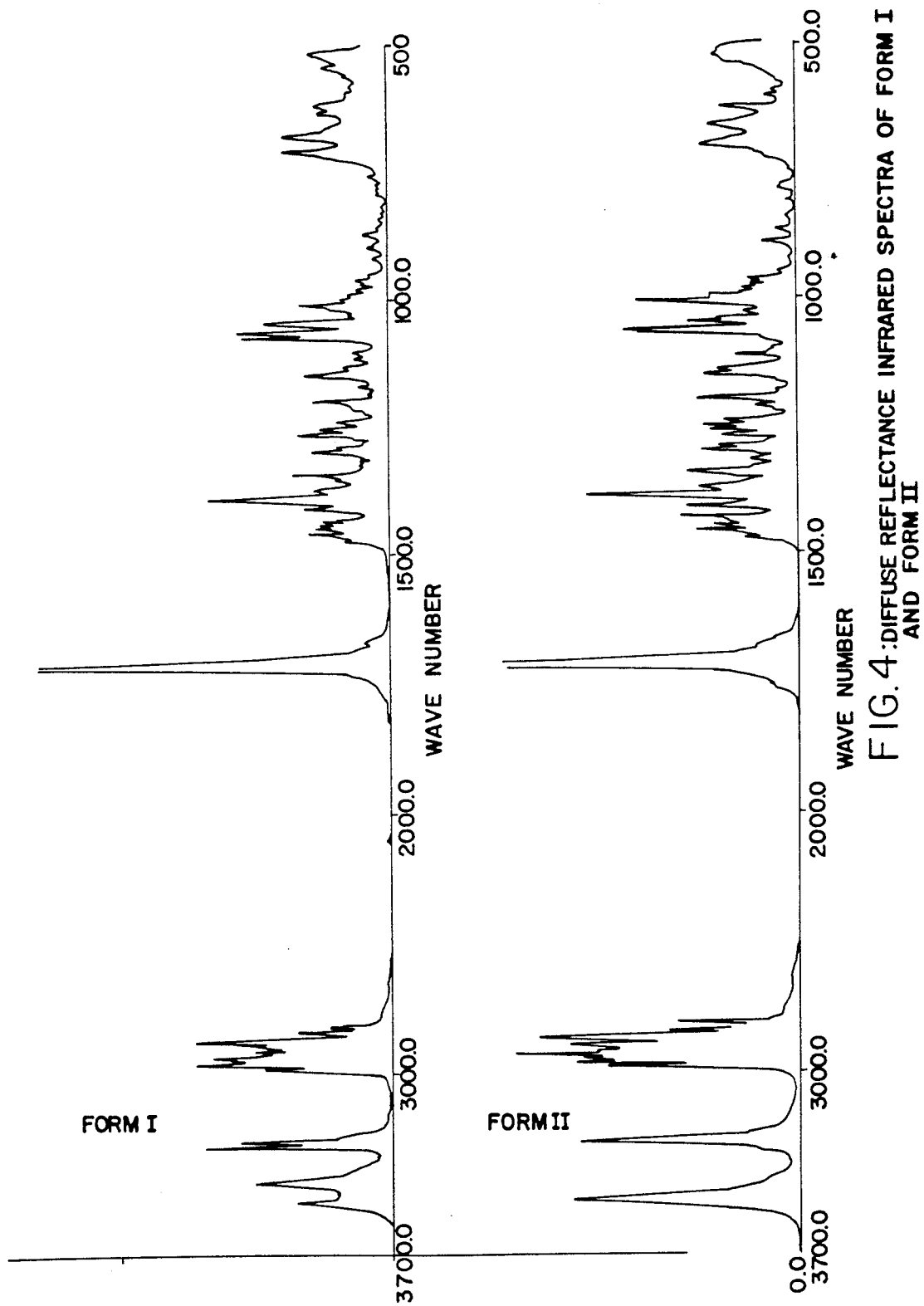

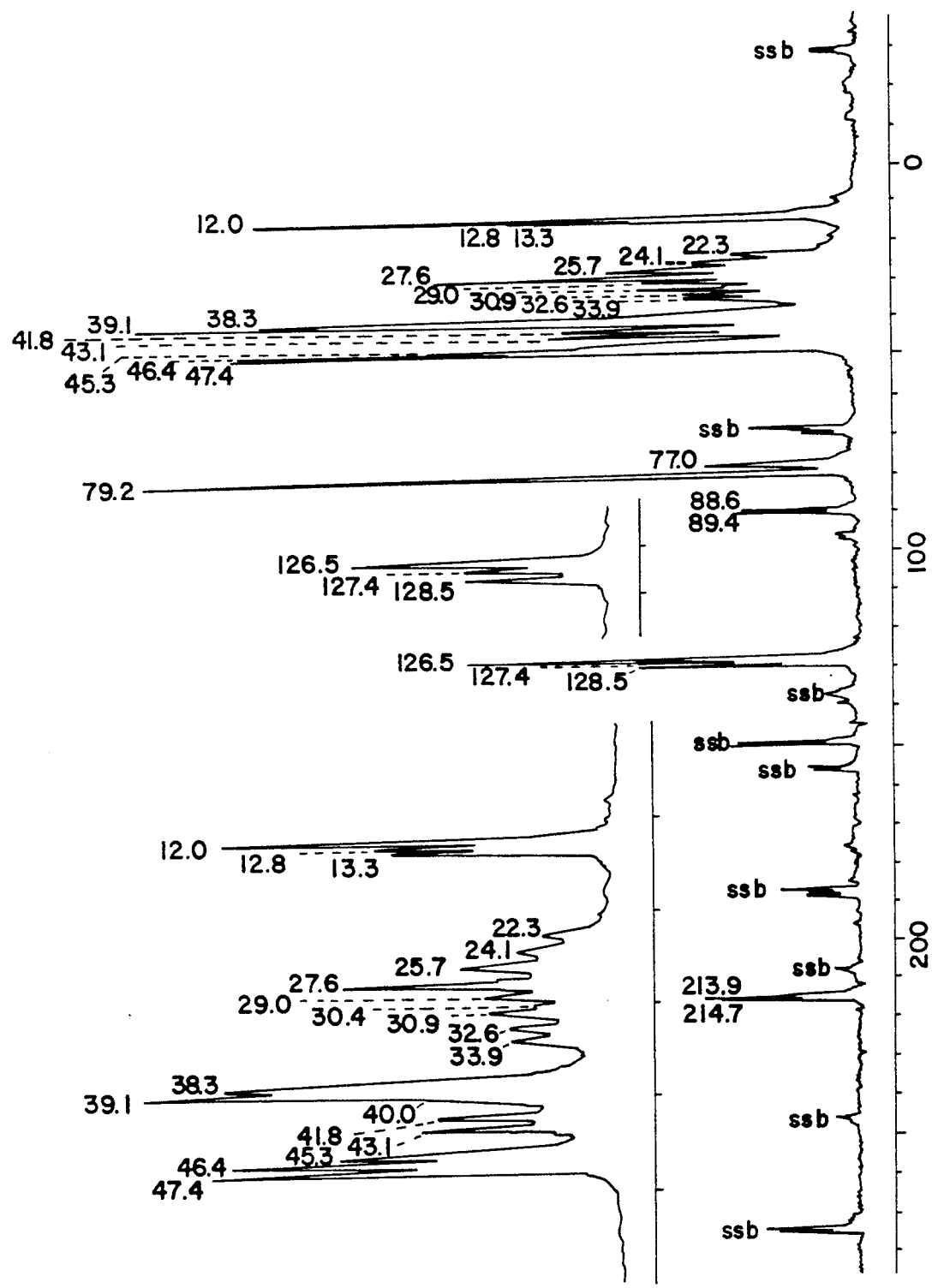
FIG.5: SOLID STATE $^{13}$C-NMR SPECTRUM OF FORM I

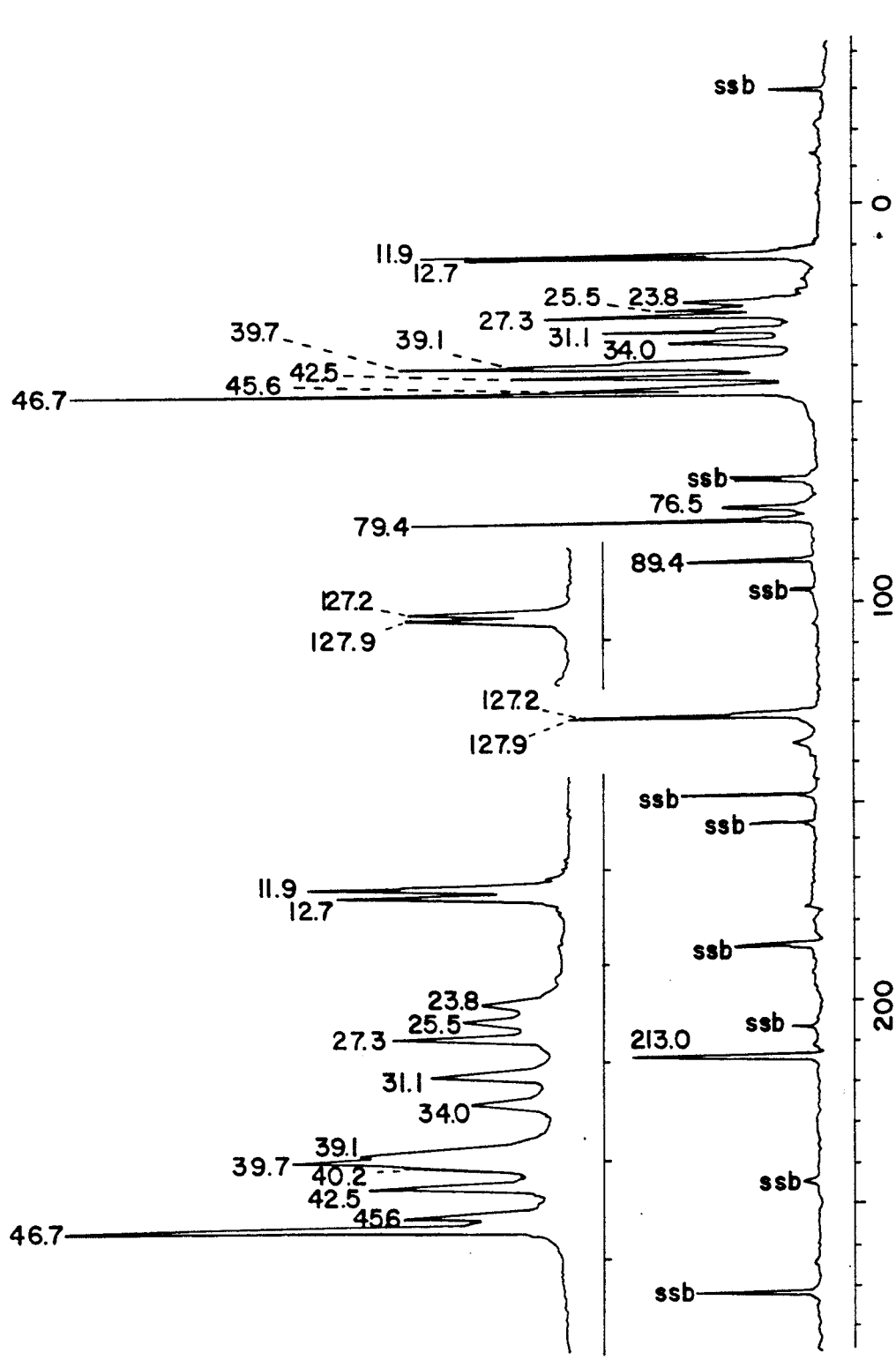

PHARMACEUTICAL COMPOSITION WHICH CONTAINS A PHARMACEUTICALLY SUITABLE CARRIER AND THE COMPOUND HAVING THE STRUCTURE (7α,17α)-17-HYDROXY-7-METHYL-19-NOR-17-PREGN-5(10)-EN-20-YN-3-ONE

The invention relates to a pharmaceutical composition which contains a pharmaceutically suitable carrier and the compound having the structure (7α,17α)-17-hydroxy-7-methyl-19-nor-17-pregn-5(10)-en-20-yn-3-one and also to a method for the preparation of this compound for use in the pharmaceutical composition.

BACKGROUND OF THE INVENTION

The compound (7α,17α)-17-hydroxy-7-methyl-19-nor-17-pregn-5(10)-en-20-yn-3-one having the structural formula 1:
is known, for example from U.S. Pat. No(s). 3,340,279 and 4,701,450. The method described in these patents leads to a compound having combined oestrogenic, progestagenic and androgenic characteristics. This compound is used in medicaments having gonadomimetic, ovulation-inhibiting or immuno-modulating action.

Surprisingly, it has now been found that the compound having the formula 1. prepared in accordance with the method described in the abovementioned patents, is polymorphous and consists of two crystalline pure forms.

SUMMARY OF THE INVENTION

It may be expected of polymorphous compounds that their biological activity is comparable or identical to the biological activities of the crystalline pure forms of which the polymorphous compound consists. Nevertheless, if the polymorphous compound is used as a medicament great drawbacks are associated therewith compared with its crystalline pure components. The differences in crystal structure can lead to a difference in physico-chemical parameters such as stability, rate of dissolution, melting point, analytical data and the like, which frequently are strongly influenced by the crystal forms in the polymorphous compound. This is all the more obvious since in practice it is virtually impossible to make each batch of a polymorphous compound exactly identical in respect of composition. As a consequence of these differences, it is frequently regarded as undesirable to incorporate polymorphous compounds in medicaments and it is sometimes demanded that only one of the crystalline pure components of the polymorphous compound is used.

The aim of the present invention is, therefore, to obtain a pharmaceutical composition which contains a crystalline pure form according to the formula 1, which is completely or virtually completely free from the other crystalline form.

The term "crystalline pure form which is virtually completely free from the other crystalline form" denotes a form which contains less than 10% and preferably less than 5% of the other crystalline form.

It has now been found that by using specific crystallization techniques two crystalline pure forms, which here are designated form I and form II respectively, can be obtained from the polymorphous compound 1.

It has moreover been found that form I is chemically appreciably more stable than the already known polymorphous compound 1. This improvement in stability yields great advantages in respect of the shelf-life of the pharmaceutical product in which form I is incorporated.

BRIEF DESCRIPTION OF THE DRAWINGS

FIG. 1 shows the powder x-ray diffraction spectrum of Form I.

FIG. 2 shows the powder x-ray diffraction spectrum of Form II.

FIG. 3 shows the powder x-ray diffraction spectrum of a mixture of Form I (57.4%) and Form II (42.5%).

FIG. 5 shows the diffuse reflectance infrared spectra of Form I and Form II.

FIG. 5 shows the solid state $^{13}$C-NMR spectrum of Form I.

FIG. 6 shows the solid state $^{13}$C-NMR spectrum of Form II.

DETAILED DESCRIPTION OF THE EMBODIMENTS

The invention relates to a pharmaceutical composition which contains a pharmaceutically suitable carrier and the compound having the structure (7α,17α)-17-hydroxy-7-methyl-19-nor-17-pregn-5(10)-en-20-yn-3-one, characterized in that the said compound is a crystalline pure or virtually pure form which is completely or virtually completely free from the other crystalline form.

A pharmaceutical composition of this type has the advantage that the reproducibility is appreciably increased and that the physical data, within acceptable limits, are always identical.

The pure crystalline compounds, and in particular the compound with form I, are suitable for treating menopausal complaints or for modulating the immune system, and also for combating osteoporosis.

Form I is obtained by crystallizing the polymorphous compound 1 from a selected polar solvent. A suitable method is to dissolve the polymorphous compound in acetone or ethanol, after which the solution is added to water. Conversely, water can also be added to a solution of the polymorphous compound in acetone or ethanol. Other suitable solvents are, for example, ethyl acetate, acetonitrile and acetone/hexane mixtures. Mixtures of methanol and water, from which only mixtures of the two crystalline forms always crystallize, are unsuitable.

Form II can be obtained by crystallizing the polymorphous compound from a selection of apolar solvents. Toluene is very suitable, as is also hexane to which a little ethyl acetate has been added. Another suitable solvent is trichloroethylene.

The rate of crystallization, which is influenced most strongly by the crystallization temperature, can also play a role in obtaining crystalline pure forms. Thus, in general good results are obtained from anhydrous acetone only when the crystallization is carried out at a relatively low temperature.

The forms I and II can be readily differentiated from one another. In particular, three methods are suitable, i.e. powder X-ray diffraction, infra-red techniques and solid state $^{13}$C-NMR spectroscopy.

Powder X-ray diffraction spectra are given in FIGS. 1, 2 and 3. FIG. 1 shows the spectrum of form I, while FIG. 2 shows the spectrum of form II. The differences are obvious. The double peaks which are obtained with form I are characteristic. The spectrum of the polymorphous compound 1, which clearly deviates from the spectra of forms I and II, is given in FIG. 3.

The diffuse reflectance infrared Fourier transform (DRIFT) spectra of forms I and II are given in FIG. 4. Here also clear differences between the two forms are discernible, the double peaks for form I in the range between 3000 and 3700 cm$^{-1}$ being striking.

The solid state $^{13}$C-NMR spectra of forms I and II respectively are given in FIGS. 5 and 6. The differences are evident and the peak duplication in the case of form I is again striking.

The three abovementioned techniques are particularly well suited for the determination of the quantity of form II in pure form I and of the quantity of form I in pure form II. In the case of powder X-ray diffraction technique, the two most intense peaks (13.7 and 17.4 degrees for form I, FIG. 1; 3.5 and 17.4 degrees for form II, FIG. 2) are compared with one another, after which the quantity of either form can be calculated with the aid of a calibration curve.

With DRIFT spectroscopy, the OH-stretching frequencies, which give a single absorption band in the case of form II and a double absorption band in the case of form I, can be compared with one another and the content can be determined, also with the aid of a calibration curve.

With solid state $^{13}$C-NMR spectroscopy the content can be determined very accurately by means of peak integration.

Each of the crystalline pure forms is mixed with a suitable pharmaceutical carrier and administered parenterally or orally, for example as a suspension, ointment, solution or emulsion, or as a solid pharmaceutical administration form, such as a tablet, pill, capsule or suppository.

The dosage schemes are the same as described in the abovementioned patents. An oral daily dose of 1–5 mg is particularly suitable for administration to humans.

A pharmaceutical composition in which form I is incorporated is preferred. A composition of this type has the additional advantage that a much better stability is obtained, so that the shelf-life, even under changing storage conditions, is notably improved.

The invention is illustrated with the aid of the following examples.

EXAMPLE 1

4.0 g of the polymorphous compound (7α,17α)-17-hydroxy-7-methyl-19-nor-17-pregn-5(10)-en-20-yn-3-one were recrystallized under nitrogen from 20 ml of acetone to which a trace of pyridine had been added. During this operation the temperature was slowly brought from room temperature to −10° C. The crystals were filtered off and washed with acetone at −20° C. and dried under vacuum at 40°–45° C. Yield 3.0 g of form I (purity according to DRIFT 94%, calculated from the relationship 3410 cm$^{-1}$/3490 cm$^{-1}$), m.p. 175°–170° C.

EXAMPLE 2

1 kg of the polymorphous compound was dissolved at 20°–25° C. in a mixture of 23 l of acetone and 6 ml of pyridine. The solution was filtered dust-free and the filter was washed twice with 1 l of acetone. At a temperature of 15°–20° C. the filtrate was poured as rapidly as possible, under nitrogen, into 25 l of dust-free distilled water, to which seed crystals of form I had been added. The suspension was cooled to 0°–5° C. and stirred for one hour at this temperature. The crystals were filtered off, washed with dust-free distilled water and dried under vacuum at 40° C. Yield 0.95 kg of form I (purity according to DRIFT 97.2%).

EXAMPLE 3

In a manner comparable to that described in Example 2, four batches of form I were obtained with a purity of, respectively, 100%, 95.2%, 93.3% and 99.2% (all determined by means of DRIFT).

EXAMPLE 4

2.3 kg of the polymorphous compound were dissolved in a mixture of 63 l of 96% ethanol and 114 ml of pyridine. This mixture was then poured as rapidly as possible, while stirring well, into a dust-free mixture of 53.5 l of water and 268 ml of pyridine at 18°–20° C., to which seed crystals of form I had been added. Rinsing was carried out with 3 l of ethanol and the mixture was stirred for 15 min at 18°–20° C. The crystals were filtered off, washed twice with a mixture of 10 l of dust-free distilled water and 2 ml of pyridine and then washed three times with 18 l of dust-free distilled water at 50° C. The crystals were dried under vacuum at 40° C. Yield 2.1 kg of form I (purity according to DRIFT 94.7%).

EXAMPLE 5

5.0 g of the polymorphous compound 1 were dissolved in 50 ml of ethyl acetate, to which a trace of pyridine had been added, at 40° C. 300 ml of hexane at about 35° C. were added while stirring vigorously, after which the mixture was cooled to 0° C. and stirred for a further 30 min. The crystals were filtered off and washed with hexane at 0° C. Yield 4.25 g of form II (purity according to DRIFT 100%).

EXAMPLE 6

A tablet having the following composition was prepared:

| | |
|---|---|
| form I (obtained in accordance with example 2) | 2.5 mg |
| starch | 10 mg |
| ascorbyl palmitate | 0.2 mg |
| magnesium stearate | 0.5 mg |
| lactose | to make up to 100 mg |

Base granules were prepared by mixing the lactose with a portion of the starch. The remainder of the starch was mixed to a slurry with water and added to the mixture. The whole was granulated and dried. These base granules were mixed with ascorbyl palmitate and form I, sieved, finely mixed with magnesium stearate and then tabletted.

EXAMPLE 7

A tablet having the same composition as in Example 6 was prepared by first mixing form I with 10% of the lactose and the ascorbyl palmitate and then mixing this mixture with the lactose, starch and starch slurry. The mixture was dried, finely mixed with magnesium stearate and tabletted.

EXAMPLE 8

A capsule having the following composition was prepared:

| | |
|---|---|
| form II (obtained in accordance with example 5) | 2.5 mg |
| starch | 10 mg |
| ascorbyl palmitate | 0.2 mg |
| magnesium stearate | 0.5 mg |
| Avicel | to make up to 100 mg |

The components were mixed with one another in the manner described in Example 6, granulated and filled into gelatin capsules.

EXAMPLE 9

From samples of forms I and II structural data were determined on an Enraf-Nonius CAD-4 diffractometer using CuKα. The structure was determined by direct methods of SHELXS86. The following data were obtained: Form I monoclinic P2$_1$, a=6.5298, b=51.205, c=6.6702 Å, β=101.526°, V=1758 Å$^3$, Z=4, D$_X$1.180 gcm$^{-3}$ μ=5 cm$^{-1}$, F(000)=680, room temperature, R=0.060 for 1831 reflections with I≧2.5σ(I). The symmetric unit contains two independent molecules. The A ring of molecule 1 is a 2β,3α half-chair and of molecule 2 a 2α,3β half-chair. The B rings of both molecules adopt a 7α,8β half-chair conformation. The C rings are both slightly distorted chairs and the D rings have a distorted 13β envelope conformation. Form II triclinic P1, a=6.5242, b=6.6773, c=10.287 Å, α=87.05, β=80.09, γ=79.17°, V=434.7 Å$^3$, Z=1, D$_x$=1.194 gcm$^{-3}$, =5.1 cm$^{-1}$, F(000)=170, room temperature, R=0.066 for 1495 reflections with I≧2.5-σ(I). The A ring has a 2α,3β half-chair conformation, the B ring a 7α,8β half-chair conformation, and the C rings adopts a slightly distorted chair conformation. The D ring is a distorted 13β envelope.

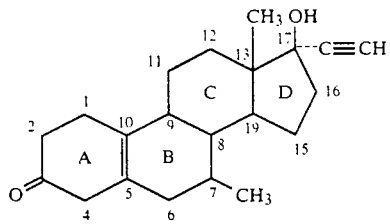

We claim:

1. A pharmaceutical composition comprising a pharmaceutically suitable carrier and a pharmaceutically effective amount of a compound having the structure (7α,17α)-17-hydroxy-7-methyl-19-nor-17-pregn-5(10)-en-20-yn-3-one, wherein said compound is defined by a powder X-ray diffraction spectrum essentially corresponding to the spectrum given in FIG. 1 and is at least 90% crystalline pure.

2. A pharmaceutical composition comprising a pharmaceutically suitable carrier and a pharmaceutically effective amount of a compound having the structure (7α,17α)-17-hydroxy-7-methyl-19-nor-17-pregn-5(10)-en-20-yn-3-one, wherein said compound is defined by a powder X-ray diffraction spectrum essentially corresponding to the spectrum given in FIG. 2 and is at least 90% crystalline pure.

3. The pharmaceutical composition according to claim 1, wherein the crystalline purity of the compound is greater than 95%.

4. A method for the preparation of a crystalline pure compound for use in a pharmaceutical composition according to claim 1, comprising dissolving the polymorphous compound in a polar solvent, mixing the resulting solution with water, and crystallizing the compound in essentially crystalline pure form.

5. A method for the preparation of crystalline pure compound for use in a pharmaceutical composition according to claim 2, comprising dissolving the polymorphous compound in an apolar solvent, and crystallizing the compound in essentially crystalline pure form.

6. The pharmaceutical composition according to claim 2, wherein the crystalline purity of the compound is greater than 95%.

7. A method of treating mammals suffering from menopausal complaints comprising administering to said mammals (7α,17α)-17-hydroxy-7-methyl-19-nor-17-pregn-5(10)-en-20-yn-3-one, defined by a powder X-ray diffraction spectrum which largely corresponds to the spectrum given in FIG. 1 or FIG. 2, in an amount sufficient for treatment.

8. A method of treating mammals suffering from immune deficiencies comprising administering to said mammals (7α,17α)-17-hydroxy-7-methyl-19-nor-17-pregn-5(10)-en-20-yn-3-one, defined by a powder X-ray diffraction spectrum which largely corresponds to the spectrum given in FIG. 1 or FIG. 2, in an amount sufficient for treatment.

9. A method of treating mammals suffering from osteoporosis comprising administering to said mammals (7α,17α)-17-hydroxy-7-methyl-19-nor-17-pregn-5(10)-en-20-yn-3-one, defined by a powder X-ray diffraction spectrum which largely corresponds to the spectrum given in FIG. 1 or FIG. 2, in an amount sufficient for treatment.

* * * * *